United States Patent
Huang

(10) Patent No.: US 8,021,354 B2
(45) Date of Patent: Sep. 20, 2011

(54) NEEDLELESS INJECTION STRUCTURE

(76) Inventor: Shu-Fang Huang, Changhua County (TW)

(*) Notice: Subject to any disclaimer, the term of this patent is extended or adjusted under 35 U.S.C. 154(b) by 47 days.

(21) Appl. No.: 12/711,365

(22) Filed: Feb. 24, 2010

(65) Prior Publication Data

US 2010/0234798 A1  Sep. 16, 2010

(30) Foreign Application Priority Data

Mar. 11, 2009  (TW) .............................. 98107818 A

(51) Int. Cl.
*A61M 25/16* (2006.01)
(52) U.S. Cl. ..................... 604/539; 251/149.1
(58) Field of Classification Search .............. 604/68, 604/537, 539, 323, 167.01, 167.02, 167, 604/256; 251/149.1, 149.3, 149.8
See application file for complete search history.

(56) References Cited

U.S. PATENT DOCUMENTS

| | | | | |
|---|---|---|---|---|
| 4,429,856 A * | 2/1984 | Jackson | ...... | 251/149.1 |
| 5,509,433 A * | 4/1996 | Paradis | ...... | 137/1 |
| 5,535,771 A * | 7/1996 | Purdy et al. | ...... | 137/15.01 |
| 5,573,516 A * | 11/1996 | Tyner | ...... | 604/249 |
| 5,806,831 A * | 9/1998 | Paradis | ...... | 251/149.1 |
| 6,808,161 B1* | 10/2004 | Hishikawa | ...... | 251/149.1 |
| 6,840,501 B2* | 1/2005 | Doyle | ...... | 251/149.1 |
| 7,691,090 B2* | 4/2010 | Belley et al. | ...... | 604/246 |

* cited by examiner

*Primary Examiner* — Nicholas D Lucchesi
*Assistant Examiner* — Quynh-Nhu H Vu
(74) *Attorney, Agent, or Firm* — Rosenberg, Klein & Lee

(57) ABSTRACT

A needleless injection structure includes a duct, a stuff base and a casing. The duct has a through channel. The duct has a ring channel and a transverse channel formed on a top thereof. The stuff base is disposed on the top of the duct. The stuff base has an uneven portion, a first fillet, a plurality of first protrusions and a closed space. The casing is assembled on the duct. The casing has an opening, a second fillet, an accommodating space and a plurality of second protrusions. The opening communicates with the accommodating space. The stuff base stays in the accommodating space. The improved needleless injection structure is provided thereby, which results in increasing the use of safety, saving the cost, and mitigating the pain of the patient.

9 Claims, 10 Drawing Sheets

NEEDLELESS INJECTION STRUCTURE

BACKGROUND OF THE INVENTION

1. Field of the Invention

The present invention relates to a needleless injection structure, in particular, to a needleless injection structure, which is applied to a medical tools for blood transfusion or infusion.

2. Description of Related Art

Referring to FIG. 1, in which a conventional duct 1a is illustrated. The conventional duct 1a, which is hollow, has an opening 11a, and a stuff 12a filled in the opening 11a. The stuff 12a is resilient. When medical professionals intend to do some drug injections, the drug is inhaled into a syringe 2a first. Piercing the needle 21 of the syringe 2a into the duct 1a and pushing a plunger 22a to force the drug into the duct 1a. However, the needle 21a is acute and possesses the hazards of infection for someone if stabbed. A needleless injection structure may be one solution to this problem. Besides, the used needles are treated as medical disposals, which is a loading to prime cost. Furthermore, the injection with the needle 21a provides the injecting act too fast to cause the discomfort of the patent.

SUMMARY OF THE INVENTION

In view of the aforementioned issues, the present invention provides a needleless injection structure for the improvement of the use of the safety. In addition, the needleless injection structure according to the preset invention can make cost saving and discomfort mitigation.

To achieve the above-mentioned objectives, the present invention provides a needleless injection structure including a duct, a stuff base and a casing. The duct has a through channel extending a top through a bottom thereof, a ring channel and a transverse channel both indented on the top thereof, wherein the transverse channel communicates the ring channel with the through channel. The stuff base is disposed on the top of the duct. The stuff base has an uneven portion, a first fillet, and a plurality of first protrusions. The uneven portion is arranged on a top of the stuff, the first protrusions are annularly disposed around an external wall of the stuff; the stuff base further includes a closed space formed therein and a buffering area arranged over the closed space. The casing is assembled on the duct. The casing has an opening, a second fillet, an accommodating space and a plurality of second protrusions. The opening communicates with the accommodating space. The second fillet corresponds to the first fillet and being with a second guide angle less than one of first fillet. The stuff base is disposed in the accommodating space. The second protrusions retain against the external wall of the duct, while the first protrusions retain against the internal wall of the casing.

The trough channel is formed in the duct; the stuff base is disposed at the top of the duct; the casing is assembled to the duct; the casing has the opening communicating the accommodating space; and the stuff base is disposed in the accommodating space are disclosed in the present invention. The following beneficial effects according to the needleless injection structure of the present invention are described as following: Needleless could improve the use of the safety and diminish the prime cost. The stuff base possesses the buffer of compression and decompression for the drug, which is good at mitigating the pain of the patient while in injection. In addition, the guiding angle of the second fillet of the casing is less than that of the first fillet of the stuff base, so that a tight fit is offered thereby in order to prevent the drug reflux.

Furthermore, the closed space is formed in the stuff base to increase the restoring capability of the stuff base. The buffering area is formed at the top of the closed space, the expansion deformation measurement of the stuff base would be decreased, which prevent the drug blocking from the over-expansion of the stuff base.

Still other aspects, features, and attendant advantages of the present invention will become apparent to those skilled in the art from a reading of the following detailed description of embodiments constructed in accordance therewith, taken in conjunction with the accompanying drawings.

DETAILED DESCRIPTION OF THE PREFERRED EMBODIMENTS

Figure 1:
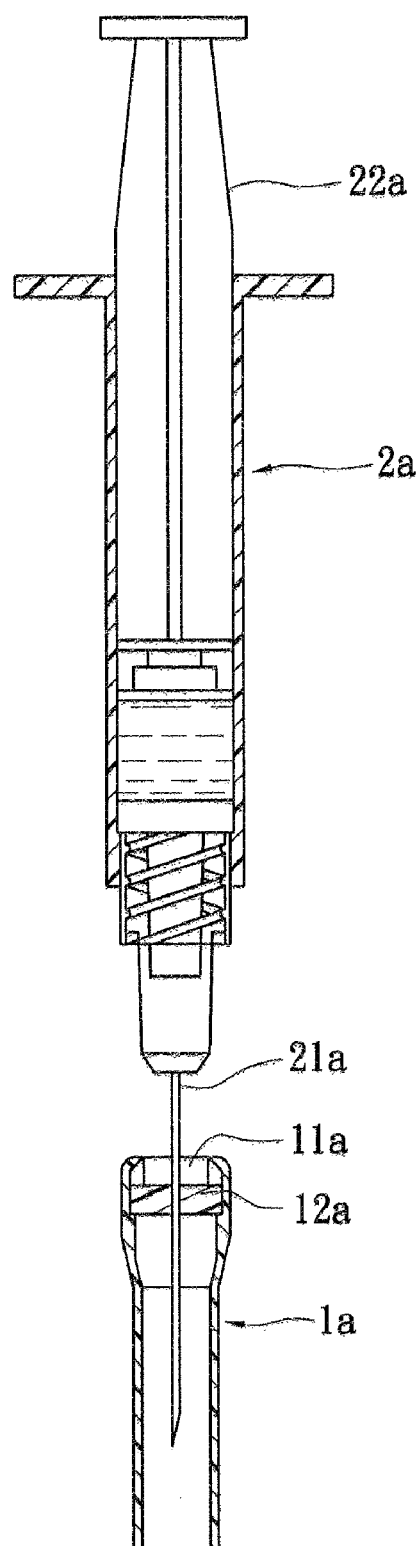
FIG. 1 is a cross-sectional view of a conventional duct in use.
Figure 2:
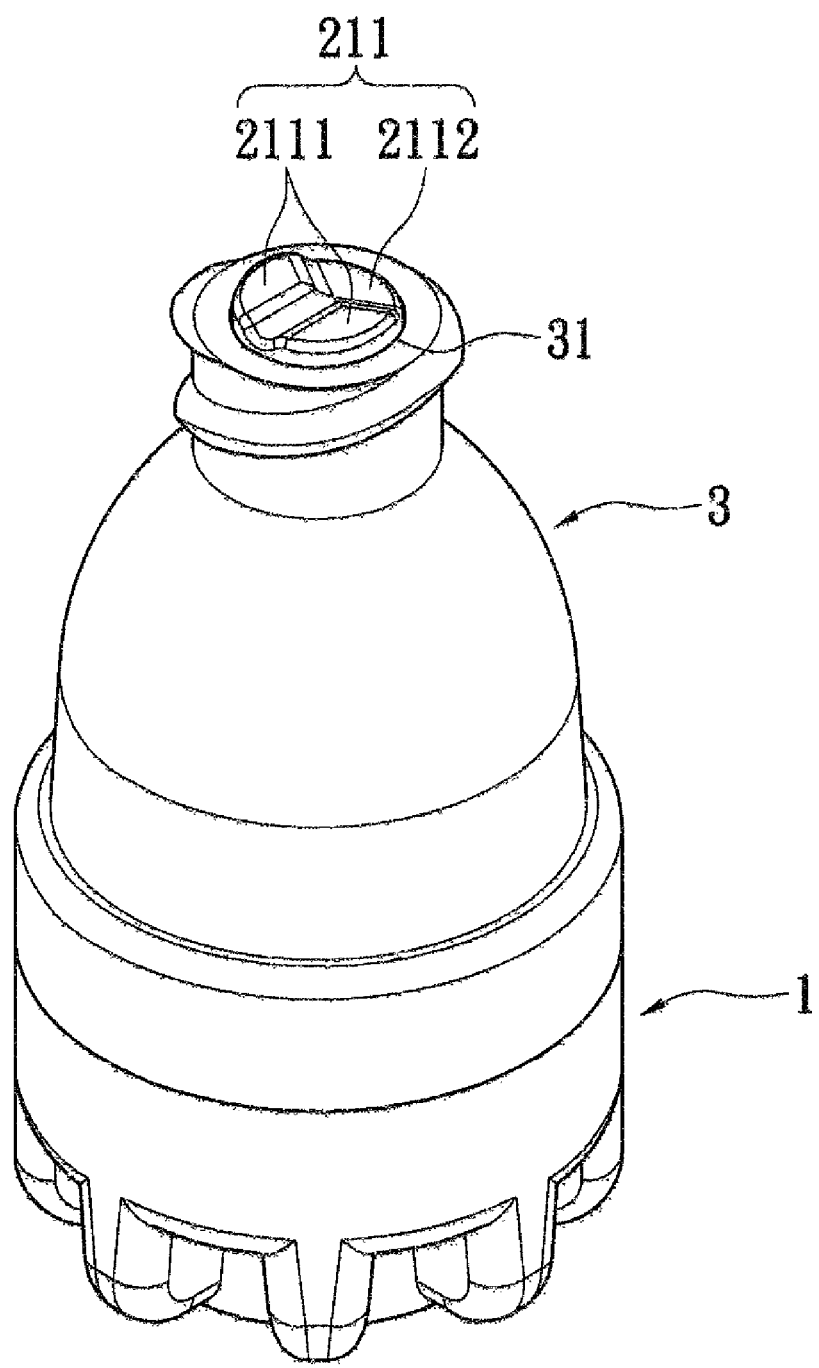
FIG. 2 is a perspective view of a needleless injection structure according to the present invention.

Referring now to FIGS. 2 to 8, in which a needleless injection structure according to the present invention is disclosed. The needleless injection structure, applied to medical tools for blood transfusion or infusion, includes a duct 1, a stuff base 2 and a casing 3. The duct 1 has a through channel 11 extending a top through a bottom thereof The duct 1 has a ring channel 12 and a strip-liked transverse channel 13 both indented on the top thereof. The duct 1 has a first connection portion 14 annularly protruding at the top thereof. The transverse channel 13 is formed within the ring channel 12 for guiding the liquid. The transverse channel 13 communicates the ring channel 12 with the through channel 11. The first connection portion 14 is disposed around the ring channel 12.

In this embodiment, the stuff base 2 can be made of silicone materials, and other resilient materials. The stuff base 2 is disposed on the top of the duct 1. The stuff base 2 has an upper section 21, a deformation section 22, a lower section 23, a closed space 24 and a bottom plate 25 (illustrated in FIGS. 3 and 7). The upper section 21 is cylindrical, and has an uneven portion 211 on a top thereof. In this embodiment, the uneven portion 211 includes two projections 2111, which are higher, and one indentation 2112, which is lower (illustrated in FIGS. 3 and 7). A slit portion, which is lower, is arranged between the two projections 2111 and communicates with the indentation 2112. In another embodiment, the uneven portion 211 includes one projection and two indentations. A first fillet 212 is arranged between the upper section 21 and the deformation section 22. The first fillet 212 has a guiding angle of 1.4. The deformation section 22 is disposed between the upper section 21 and the lower section 23. The deformation section 22 includes a flange 221 annularly arranged thereof, and the flange 221 abuts against an internal wall of the casing 3 to prevent the drug reflux. The lower section 23 includes a plurality of first protrusions 231 disposed on the periphery thereof with intervals. In this preferred embodiment, the first protrusions 231 are elongated protruding strips to abut against the internal wall of the casing 3 for engaging the stuff base 2 into the casing 3. The closed space 24 is formed in the stuff base 2 and the pressure therein is about 1 atm. A buffering area 241 arranged on a top of the closed space 24 to be pen-point-shaped. The bottom plate 25 is arranged at a bottom of the lower section 23.

Figure 10:
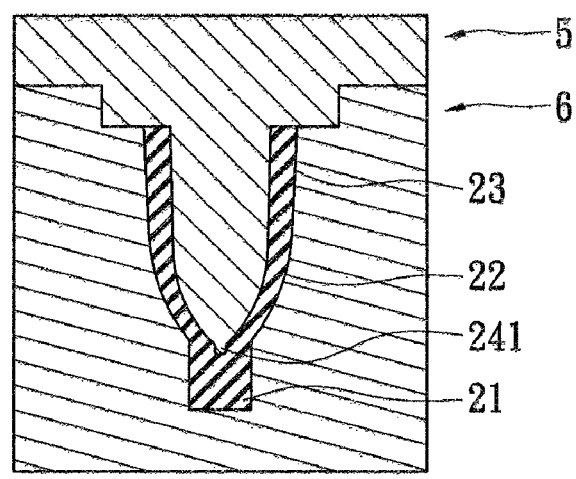
FIG. 10 is a cross-sectional view of the stuff base at the second stage according to the present invention.
Figure 11:
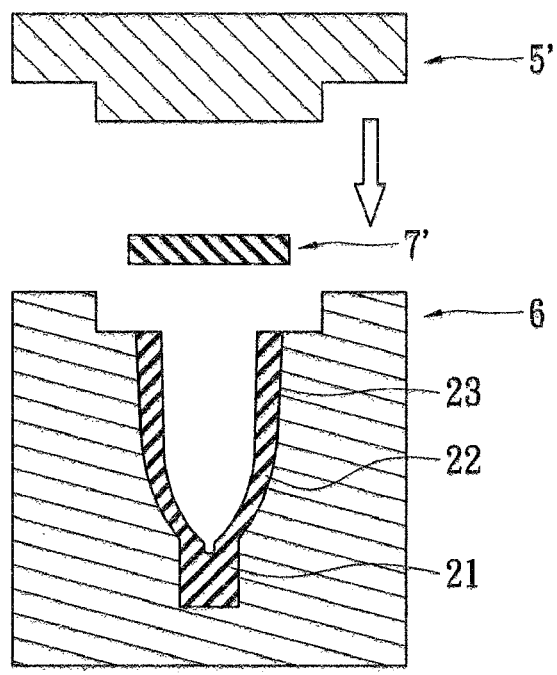
FIG. 11 is a cross-sectional view of the stuff base at the third stage according to the present invention.
Figure 12:
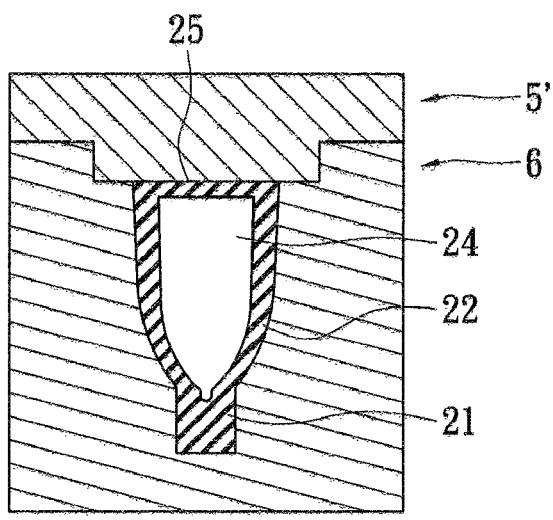
FIG. 12 is a cross-sectional view of the stuff base at the fourth stage according to the present invention.
Figure 13:
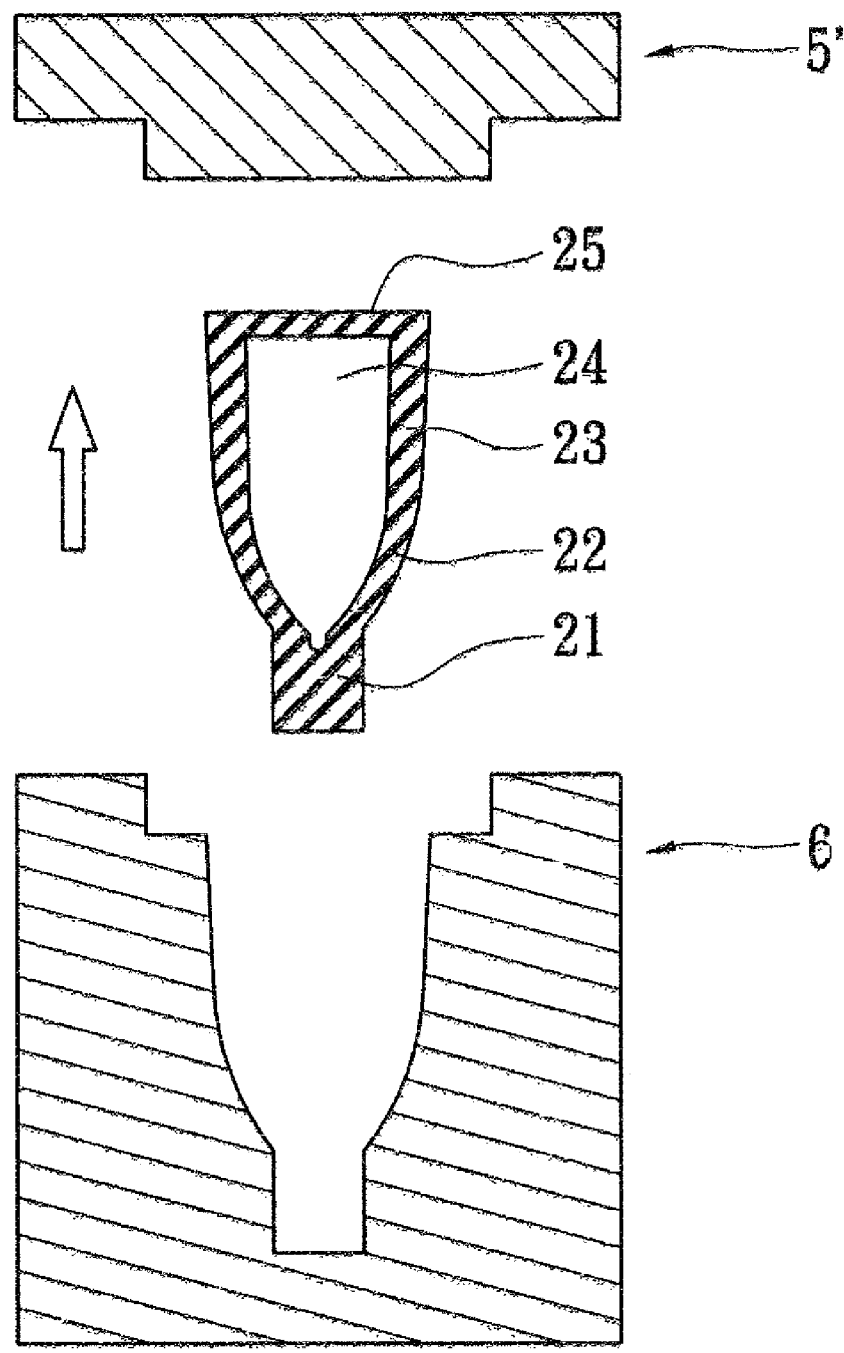
FIG. 13 is a cross-sectional view of the stuff base at the fifth stage according to the present invention.

With respect to FIGS. 9 to 13, the upper section 21, the deformation section 22, the lower section 23 and the buffering area 241 of the stuff base 2, which is worthy to mention, is to utilize an upper mold 5, a lower mold 6 to make a silicon member 7 deformed at a first deformation stage, illustrated in FIG. 10. The closed space 24 and the bottom plate 25 of the stuff base 2 is deformed via another upper mold 5' and further silicon member 7' at a second deformation stage, illustrated in FIG. 12. The bottom plate 25 is welt to the lower section 23, and the stuff base 2 is done after ejection, illustrated in FIG. 13.

Figure 3:
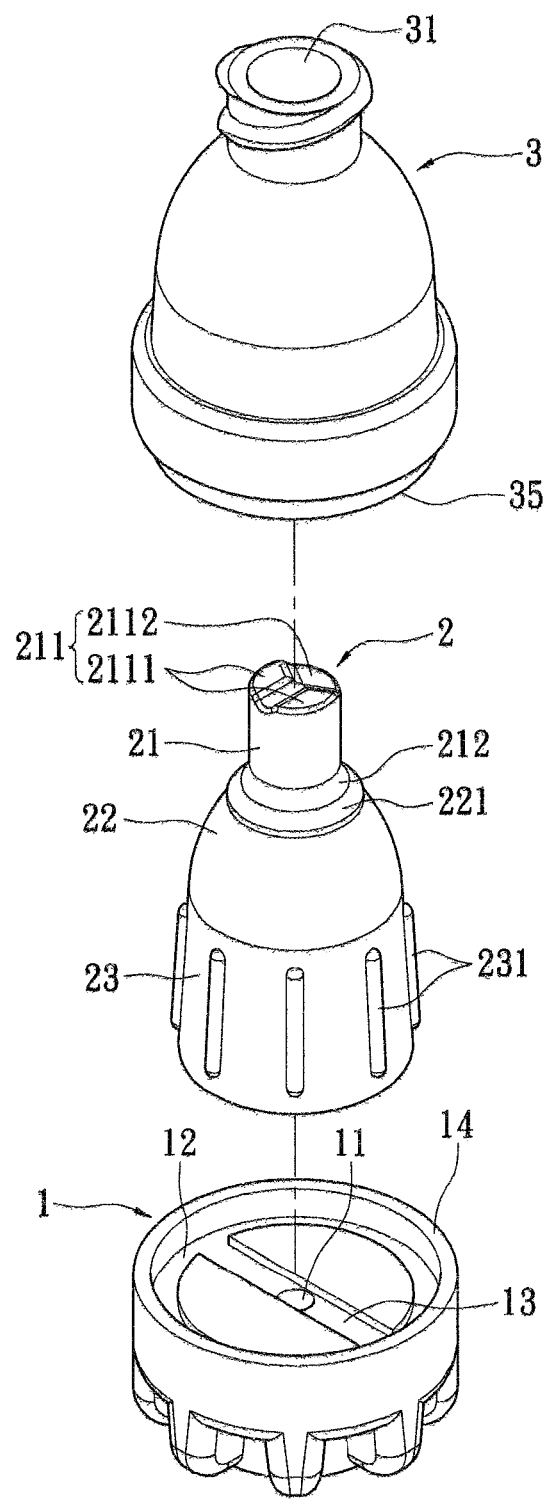
FIG. 3 is a perspective exploded view of the needleless injection structure according to the present invention.
Figure 4:
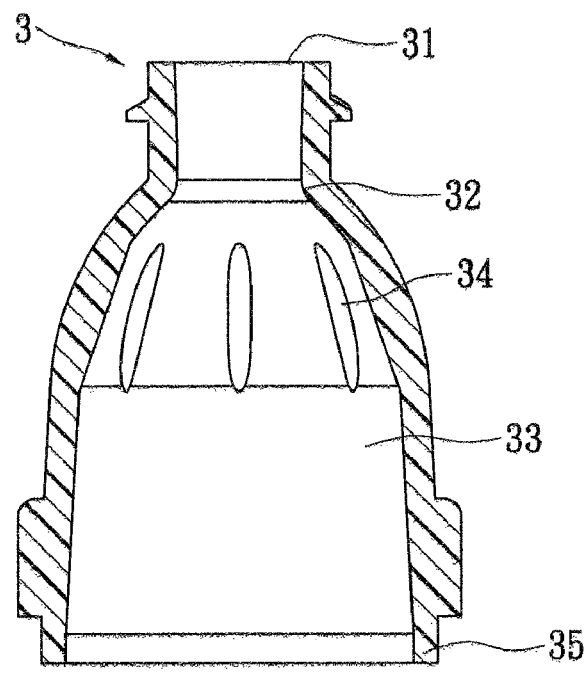
FIG. 4 is a cross-sectional view of a casing of the needleless injection structure according to the present invention.
Figure 7:
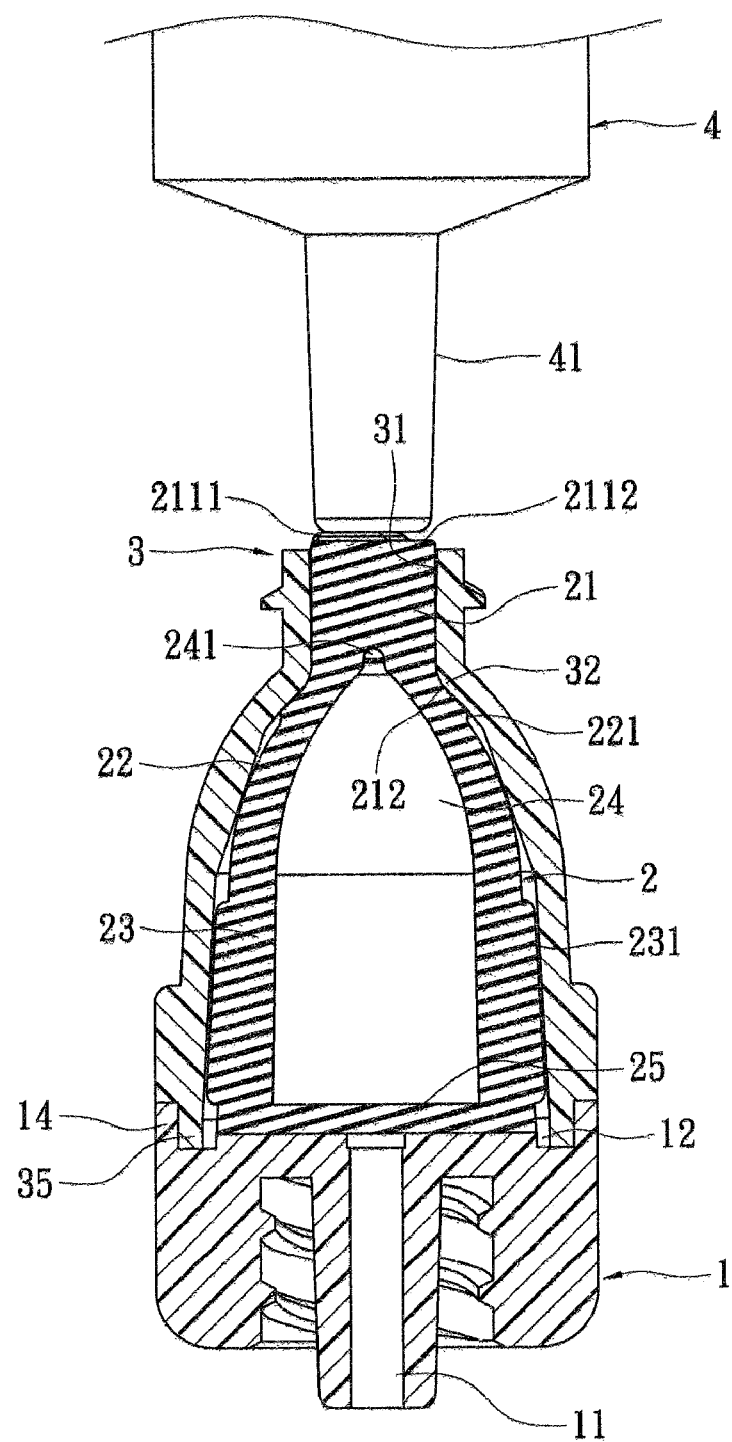
FIG. 7 is a cross-sectional view of the needleless injection structure before the puncture of the syringe.

Reference is made to FIG. 3. The casing 3 is made of plastic materials. The casing 3 has an opening 31, a second fillet 32, an accommodating space 33, a plurality of second protrusions 34 and a second connection portion 35. The opening 31 communicates with the accommodating space 33. The second fillet 32 corresponds to the first fillet 212 and with a second guide angle less than the first guiding angle of the first fillet 212 for fitting with each other. In this preferred embodiment, the second guiding angle is 1.0. The stuff base 2 is disposed in the accommodating space 33. The upper section 21 partially extends out of the opening 31 of the casing 3, as shown in FIG. 7. The second protrusions 34 are protruding strips elongated and arranged around the internal wall of the casing 3. The second protrusions 34 abut against the deformation section 22 of the stuff base 2. The second connection portion 35 is annularly arranged at the bottom of the casing 3. The first connection portion 14 is assembled to the second connection portion 15 via threads or other interference fits. The second connection portion 35 extends into the ring channel 12, illustrated in FIG. 7.

Figure 5:
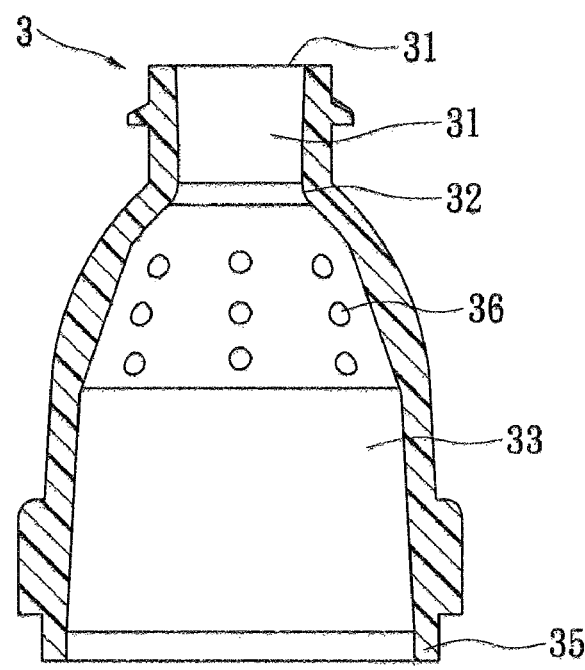
FIG. 5 is a cross-sectional view of another embodiment of the casing according to the present invention.

With respect to FIG. 5, in which a cross-sectional view of another embodiment of the casing. The points are the second protrusions 36 of the casing 3 are bumps.

Figure 6:
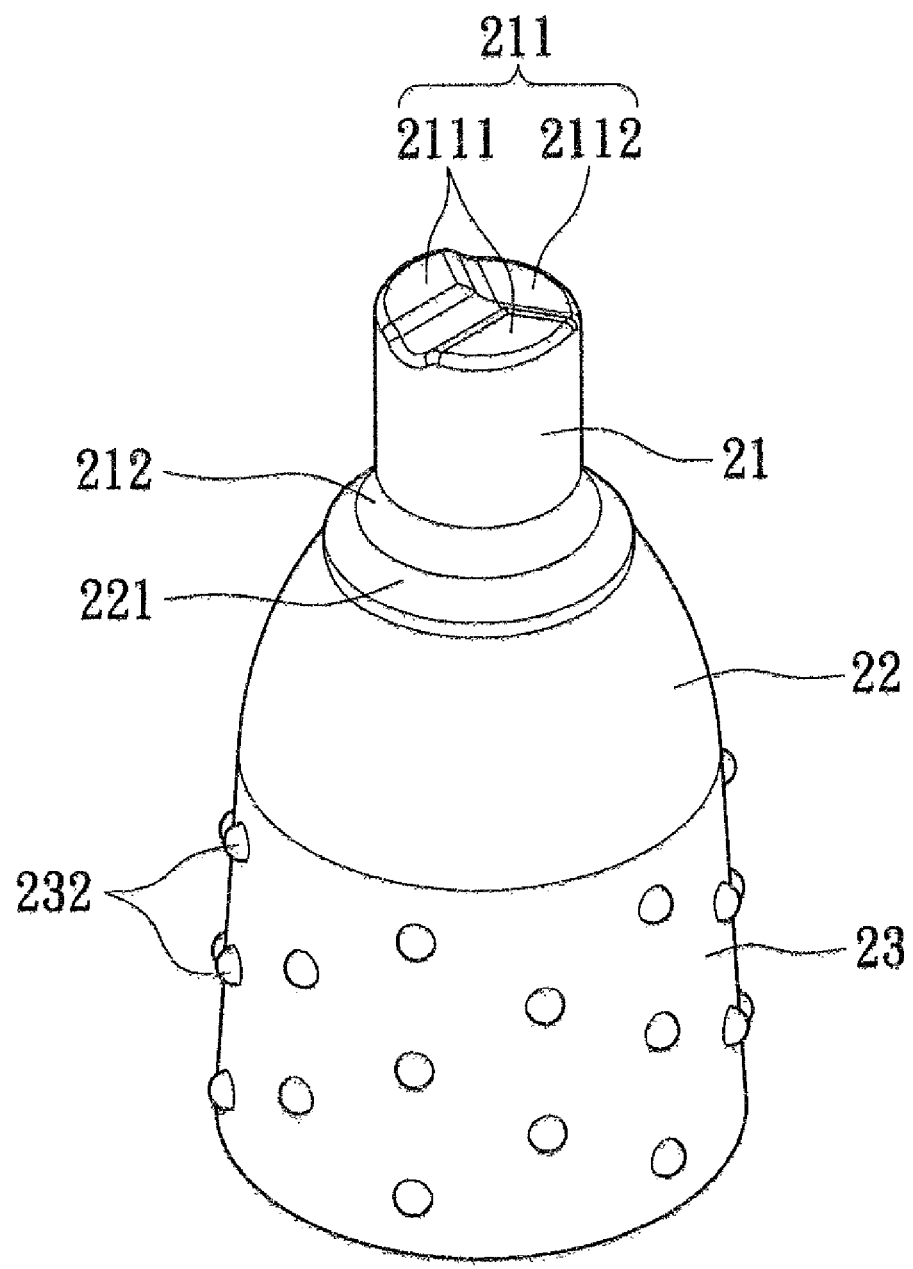
FIG. 6 is a cross-sectional view of another embodiment of the stuff base according to the present invention.

With respect to FIG. 6, in which a respective view of another embodiment of the stuff base. The points are the first protrusions 232 of the stuff base 2 are bumps.

Figure 8:
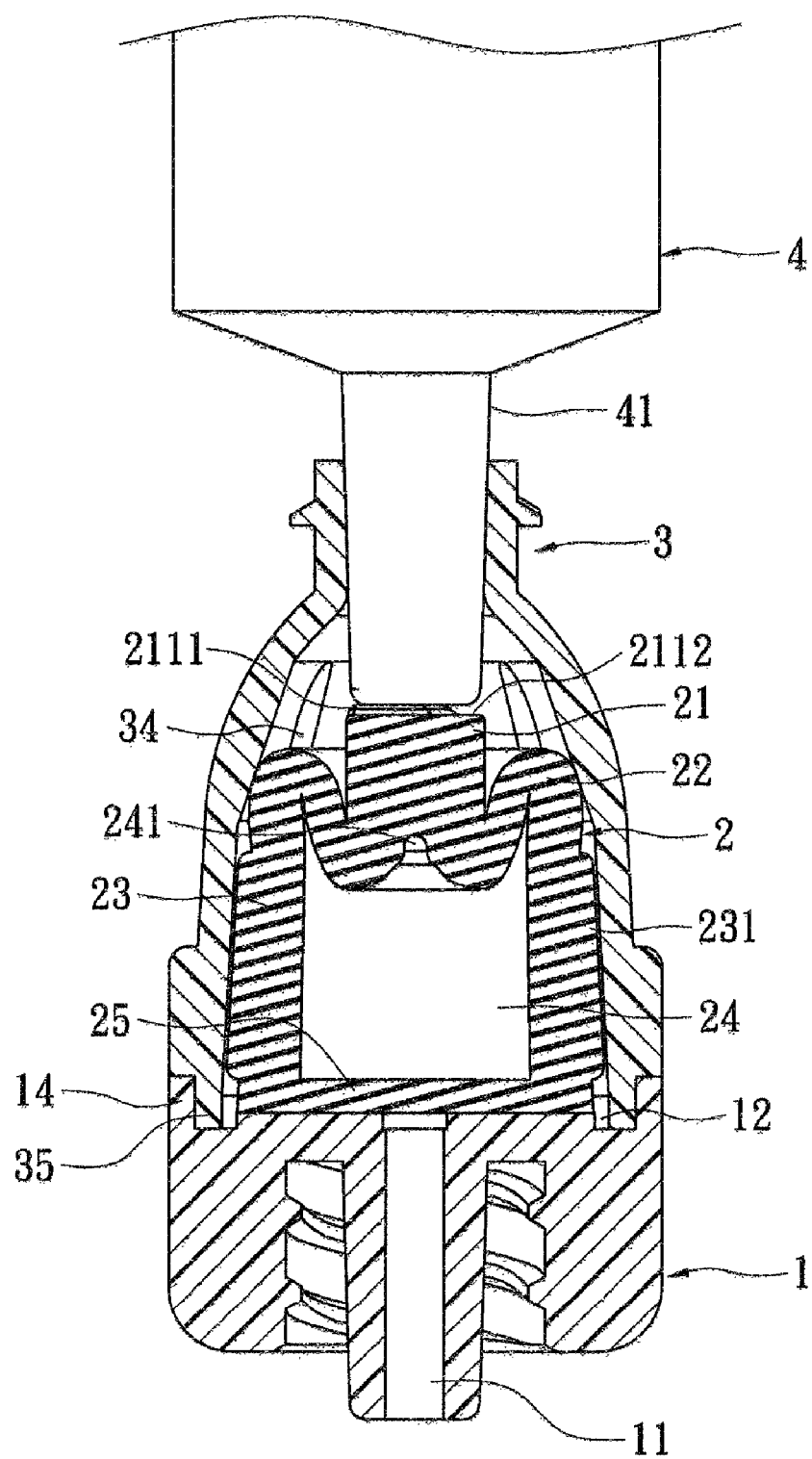
FIG. 8 is a cross-sectional view of the needleless injection structure after the puncture of the syringe.
Figure 9:
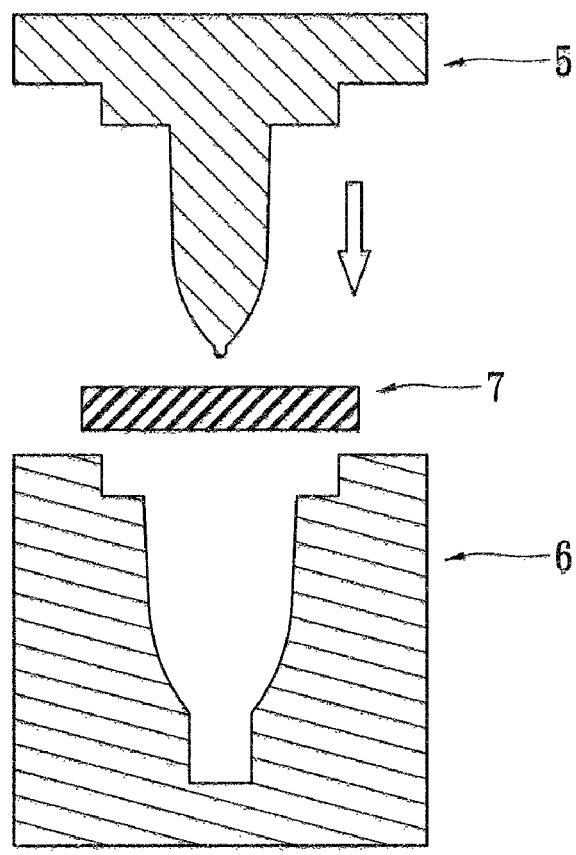
FIG. 9 is a cross-sectional view of the stuff base at the first stage according to the present invention.

With respect to FIGS. 7 and 8, when an injection head 41 of a syringe 4 inserts into the casing 3 via the opening 31. The injection head 41 would propel the two projections 2111 forcing the upper section 21 downwardly, The deformation section 22 is pushed and deformed. The drug in the syringe 4 thereby would flow into the casing 3 easily via the slit portion between the two projections 2111 and the indentation 2112. The drug follows the splits among the second protrusions 34 of the casing 3 and the splits among the first protrusions 231 of the stuff base 2, in order to flow into the ring channel 12 of the duct 1. Due to the guiding of the transverse channel 13, the drug residues of the duct 1 is decreased. The drug flows into the channel 11 and goes to human body. When the syringe 4 is pulled out of the casing 3, the stuff base 2 will restore back its original status by the elastic restoring capability per se.

The needleless injection structure according to the present invention is disclosed. The through channel 11 is formed in the duct 1. The stuff base 2 is disposed at the top of the duct 1. The stuff base 2 has the uneven portion 211, the first fillet 212 and the first protrusions 231. The closed space 24 is formed in the stuff base 2. The casing 3 is assembled to the duct 1. The casing 3 has the opening 31 communicating the accommodating space 33; and the stuff base 2 is disposed in the accommodating space 33. The following beneficial effects according to the needleless injection structure of the present invention are described as follows. Needleless function could improve the use of the safety and diminish the prime cost. The stuff base 2 possesses the buffer of compression and decompression for the drug, which is good at mitigating the pain of the patient while in injection. In addition, the guiding angle of the second fillet 32 of the casing 3 is less than that of the first fillet 212 of the stuff base 2, and the flange 221 of the deformation section 22 retain against the internal wall of the casing 3; so that a tight fit is offered thereby in order to prevent the drug reflux. Furthermore, the closed space 24 is formed in the stuff base 2 to increase the restoring capability of the stuff base 2. Due to the buffering area 241 formed at the top of the closed space, the deformation measurement of the stuff base 2 could be shared by the buffering area 241. Both of the decrease of the expansion deformation measurement of the stuff base 2 and the abutment between the second protrusions 34 of the casing 3 and the deformation section 22 could prevent the drug blocking from the over-expansion of the stuff base 2.

The above-mentioned descriptions represent merely the preferred embodiment of the present invention, without any intention to limit the scope of the present invention thereto. Various equivalent changes, alternations or modifications based on the claims of present invention are all consequently viewed as being embraced by the scope of the present invention.

What is claimed is:

1. A needleless injection structure comprising:
   a duct having a through channel extending a top through a bottom thereof, and a ring channel and a transverse channel both indented on the top thereof, wherein the transverse channel communicates the ring channel with the through channel;
   a stuff base disposed on the top of the duct, the stuff base having an uneven portion, a first fillet, and a plurality of first protrusions; wherein the uneven portion is arranged on a top of the stuff, the first protrusions are annularly disposed around an external wall of the stuff; the stuff base further includes a closed space formed therein and a buffering area arranged over the closed space; and
   a casing assembled on the duct; the casing having an opening, a second fillet, an accommodating space and a plurality of second protrusions; wherein the opening communicates with the accommodating space; the second fillet corresponding to the first fillet and being with a second guide angle less than one of first fillet; the stuff base is disposed in the accommodating space; the second protrusions retain against the external wall of the duct, while the first protrusions retain against the internal wall of the casing.

2. The needleless injection structure according to claim 1, wherein the stuff base includes an upper section, a lower section, and a deformation section connecting the upper section and the lower section; the upper section partially extends out of the opening of the casing; the uneven portion is disposed on a top of the upper section, the first fillet is arranged between the upper and the deformation sections, the first protrusions are annularly arranged around the lower section.

3. The needleless injection structure according to claim 2, wherein the deformation section includes a flange annularly arranged, the flange abuts against the internal wall of the casing.

4. The needleless injection structure according to claim 1, wherein the uneven portion includes two projections and one indentation.

5. The needleless injection structure according to claim 1, wherein the uneven portion includes one projection and two indentations.

6. The needleless injection structure according to claim 1, wherein the buffering area is pen-point-shaped.

7. The needleless injection structure according to claim 1, wherein the first protrusions of the stuff base are protruding strips, and the second protrusions of the stuff base are protruding strips.

8. The needleless injection structure according to claim 1, wherein the first protrusions of the stuff base are bumps, and the second protrusions of the stuff base are protruding bumps.

9. The needleless injection structure according to claim 1, wherein the duct includes a first connection portion at the top thereof, the casing includes a second connection portion at the bottom thereof; the first connection portion is assemblied to the second connection portion, and the second connection portion extends into the ring channel.

* * * * *